United States Patent
Sen et al.

(10) Patent No.: US 9,470,675 B2
(45) Date of Patent: Oct. 18, 2016

(54) SENSOR COMPOSITION FOR ACETONE DETECTION IN BREATH

(71) Applicant: Council of Scientific & Industrial Research, New Delhi (IN)

(72) Inventors: Amarnath Sen, Kolkata West Bengal (IN); Subhasis Rana, Kolkata West Bengal (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 14/356,127

(22) PCT Filed: Mar. 4, 2013

(86) PCT No.: PCT/IN2013/000120
§ 371 (c)(1),
(2) Date: May 2, 2014

(87) PCT Pub. No.: WO2013/164836
PCT Pub. Date: Nov. 7, 2013

(65) Prior Publication Data
US 2015/0301020 A1    Oct. 22, 2015

(30) Foreign Application Priority Data
Apr. 30, 2012 (IN) .......................... 1313/DEL/2012

(51) Int. Cl.
| | |
|---|---|
| G01N 33/497 | (2006.01) |
| G01N 33/48 | (2006.01) |
| G01N 33/00 | (2006.01) |
| B01J 19/10 | (2006.01) |
| B01J 19/08 | (2006.01) |
| A61B 5/083 | (2006.01) |
| G01N 33/64 | (2006.01) |
| A61B 5/08 | (2006.01) |
| A61B 5/145 | (2006.01) |

(52) U.S. Cl.
CPC ............. *G01N 33/497* (2013.01); *A61B 5/082* (2013.01); *A61B 5/083* (2013.01); *B01J 19/10* (2013.01); *G01N 33/64* (2013.01); *A61B 5/14532* (2013.01); *G01N 2033/4975* (2013.01)

(58) Field of Classification Search
CPC .. G01N 33/497; G01N 33/483; G01N 33/48; G01N 33/00; B01J 19/10; B01J 19/08; B01J 19/00; Y10T 436/202499; Y10T 436/200833; Y10T 436/20; Y10T 436/00
USPC ......................................... 436/130, 128, 127
See application file for complete search history.

(56) References Cited

PUBLICATIONS

Biswal, Ramesh Chandra; "Pure and Pt-loaded gamma iron oxide as sensor for detction of sub ppm level of acetone"; Sensors and Actuators B: Chemical: International Journal Devoted to Reseach and Development of Physical and Chemical Transducers, Elsevier A.A., Switzerland, vol. 157, No. 1; Mar. 23, 2011; pp. 183-188.

Sinha, Writwik; "Semiconductor Sensors for Detection of Low Concentrations of Alcholhol and Acetone Vapour"; Dissertation submitted in partial fulfillment of the requirements for the degree of Master of Technology in Nano Science & Technology, School of Materials Science and Nanotechnology Jadvapur University, Jan. 1, 2010, pp. 1-102.

International Search Report and Written Opinion of PCT/IN2013/000120 dated Feb. 12, 2014.

*Primary Examiner* — Christine T Mui
(74) *Attorney, Agent, or Firm* — Bryan D. Zerhusen; Locke Lord LLP

(57) ABSTRACT

The present invention provides a composition for acetone detection and a process of preparation thereof. The composition comprises γ-ferric oxide ($\gamma$-$Fe_2O_3$), antimony (Sb) salt, and platinum (Pt). The sensor fabricated using the said composition is selective to low concentration of breath acetone, the biomarker of diabetes, in presence of high amount of moisture normally present in breath. Such semiconductor sensors for diabetes monitoring are inexpensive, rugged, patient-friendly and on the top, non-invasive.

12 Claims, 2 Drawing Sheets

SENSOR COMPOSITION FOR ACETONE DETECTION IN BREATH

CROSS-REFERENCE TO RELATED APPLICATIONS

Figure 1:
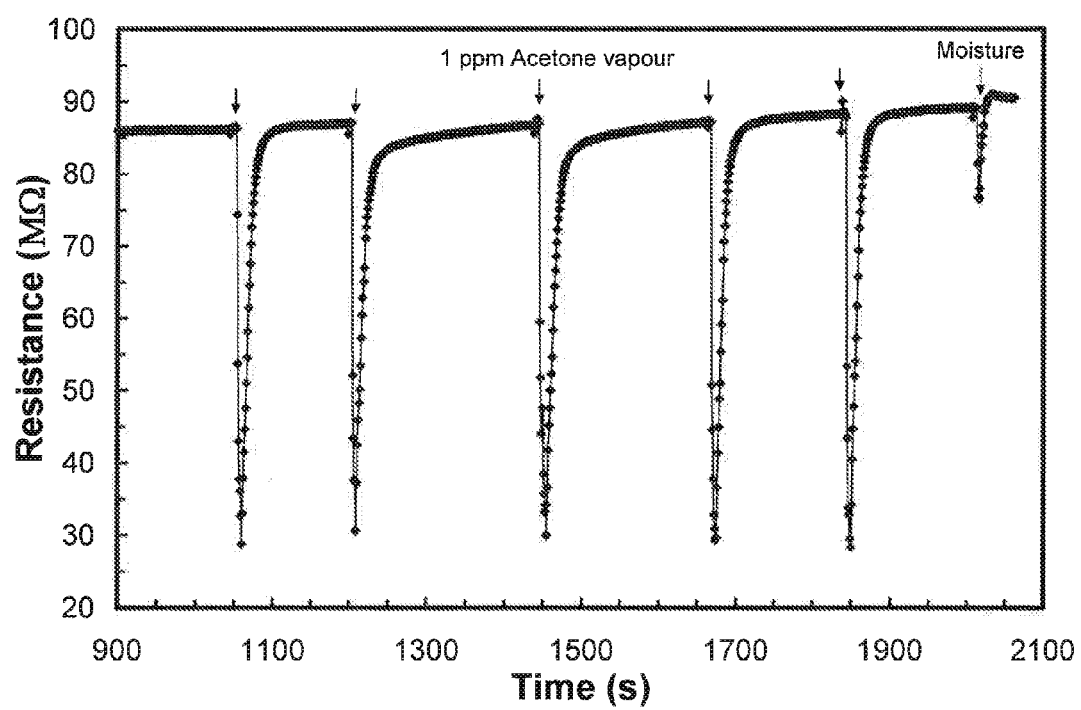

This application is the national phase under 35 U.S.C. §371 of PCT International Application No. PCT/IN2013/000120, filed Mar. 4, 2013, which claims the benefit of Indian Patent Application No. 1313/DEL/2012, filed Apr. 30, 2012, the entire contents of the aforementioned applications are hereby incorporated herein by reference.

FIELD OF THE INVENTION

The present invention relates to the field of diagnostic methods and composition. More particularly, it relates to a composition for acetone detection. More specifically, it relates to a composition for acetone detection in breath useful for diabetic diagnostics and a process of preparation thereof. The composition of the present invention comprises γ-ferric oxide (γ-$Fe_2O_3$), antimony (Sb) salt, and platinum (Pt).

BACKGROUND OF THE INVENTION

The menace of diabetes is all pervading across the globe and with the growing rate of diabetic patients. India is going to be the capital of diabetes soon. However, an early detection of diabetes can lower the potential dangers of the killer disease. Blood sugar monitoring (Fasting plasma glucose and Oral glucose tolerance test) is a time-tested reliable method of diabetes detection. However, the process is expensive, and on the top, an invasive one. To get around the problem, different non-invasive and minimally-invasive techniques like IR spectroscopy, optical rotation of polarized light, radio wave impedance, analysis of tear, analysis of fluid extracted from skin and biosensors to monitor diabetes from a drop of blood have been studied. So far, no non-invasive household gadget is available in the market for monitoring diabetes.

Many different non-invasive and minimally invasive techniques (as mentioned above) so far have been attempted to monitor diabetes [1,2]. Incidentally, it has been known for a long time that the acetone concentration in human breath increases in diabetic patients. it has been given that acetone concentration of <0.9 ppm in breath can be taken as normal for a healthy individual and concentration >1.7 ppm indicates diabetes [1,2]. There is also a good correlation between breath acetone concentration and blood sugar level [3]. Most studies on breath acetone measurements have been performed on highly sophisticated instruments like GC-MS, SFFT-MS and cavity ring down spectroscopy [4,5]. Other methods are C-13 labelled pyruvic acid-based measurements (U.S. Pat. No. 7,118,919 B2, U.S. Pat. No. RE38,575 E and WO1999/56790 A2), ion mobility spectrophotometer (U.S. Pat. No. 6,794,645 B2), microplasma in combination with spectrometer (U.S. Pat. No. 7,417,730 B2, US2004/137637 A1) [6,7] etc. Incidentally, metal oxide semiconductors like $SnO_2$, $WO_3$, ZnO and $TiO_2$ have recently been studied for low concentration acetone detection (WO2011/068976 A1) [7-20] as semiconductor sensors are inexpensive, rugged and handy. For example, Ag nanoparticles-modified $TiO_2$ sensor has 10 ppm detection limit of acetone vapour [8] and ZnO nanowires and dumbbell-like ZnO microcrystals have acetone detection limits down to 5 ppm and 1 ppm, respectively [14,15]. The sub-ppm acetone sensitivity using undoped or doped γ-$Fe_2O_3$ sensor at moderate working temperature of 150° C. has been reported earlier [1,9]. A 10 mol % $SiO_2$ doped ε-$WO_3$ composition showed an adequate sensitivity in low concentrations (100 ppb to 900 ppb) of acetone vapour at a working temperature of 400° C. [20].

The drawbacks of the so far studied metal oxide semiconductor sensors are:
 i) The sensitivity for detecting the acetone concentration in the low ppm or sub-ppm range is not high enough for making devices.
 ii) The prior art reported sensors are moisture sensitive and hence are not selective to acetone in presence of high moisture (normally present in breath).

Considering the drawbacks of the prior art sensors, the present inventors have developed the composition which overcome such drawbacks of the prior art sensors. The sensors fabricated using claimed composition shows appreciable sensitivity at ~1 ppm acetone concentration and high selectivity, and are at the same time insensitive to high amount of moisture present in breath.

OBJECTIVES OF THE INVENTION

The main object of the present invention is to provide a composition for acetone detection and a process of preparation thereof.

Another object of the present invention is to provide an improved composition for low concentration acetone detection (~1 ppm) in breath and a process of preparation thereof.

Another object of the present invention is to provide a metal oxide semiconductor-based composition for low concentration selective detection of acetone in breath in presence of high amount of moisture in breath and a process of preparation thereof.

Still another object of the present invention is to provide a metal oxide semiconductor based composition for low concentration acetone detection in breath in presence of high amount of moisture in breath and a process of preparation thereof useful for diabetic diagnostics.

SUMMARY OF THE INVENTION

The present invention provides a composition for acetone detection in breath and a process of preparation thereof The said composition for acetone detection comprises γ-ferric oxide (γ-$Fe_2O_3$), antimony (Sb) salts, and platinum (Pt). The composition shows appreciable sensitivity at ~1 ppm acetone concentration and is insensitive to high amount of moisture normally present in breath. The present invention provides a composition for acetone detection in breath for diabetics.

BRIEF DESCRIPTION OF THE DRAWINGS AND TABLES

FIG. 1. Represents the response of γ-$Fe_2O_3$-based sensors of Example 1 towards 1 ppm acetone vapour in air (RH ~45%) and saturated moisture at the operating temperature of 300° C.

Figure 2:
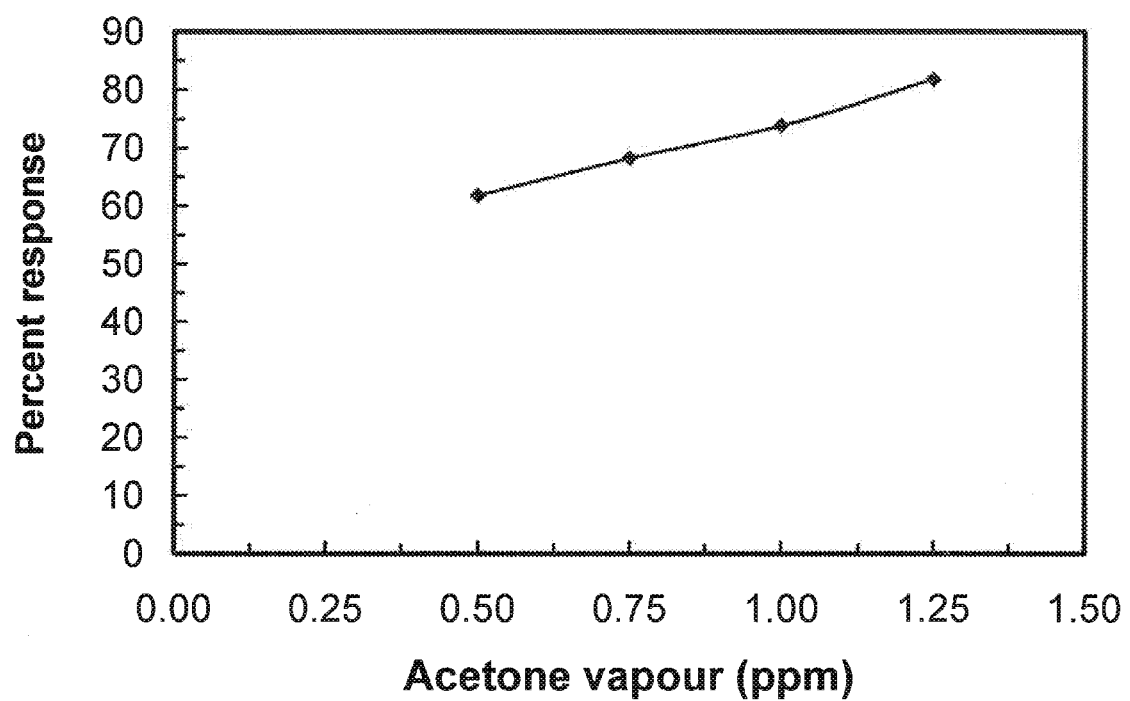

FIG. 2. Represents the percent response of γ-$Fe_2O_3$-based sensors of Example 1 towards different concentrations of acetone vapours in air (RH ~45%) at an operating temperature of 300° C.

Table 1, Data showing gas sensing characteristics of γ-$Fe_2O_3$-based sensors towards 1 ppm acetone vapour in air (RH ~45%) and 1 ppm acetone vapour in saturated moisture at an operating temperature of 300° C.

DETAILED DESCRIPTION

Accordingly, the present invention provides a composition for acetone detection comprising γ-ferric oxide (γ-$Fe_2O_3$), antimony (Sb) salt, and platinum (Pt).

One embodiment of the invention provides a composition for acetone detection comprising γ-ferric oxide, antimony salt and platinum.

In another aspect of the present invention, antimony salt is incorporated in an oxide, carbonate, nitrate, or any other salt form.

In another aspect of the present invention, platinum is incorporated in a metallic form, chloride, nitrate, or any other salt form.

In another aspect of the present invention, γ-ferric oxide concentration is in the range of 87.5-95.7 wt %.

In another aspect of the present invention, antimony salt concentration is in the range of 2.9-9.9 wt %.

In another aspect of the present invention, platinum concentration is in the range of 0.5-2.6 wt %.

In another embodiment of the present invention, the composition is prepared through sonochemical method comprising the steps of:
  (a) preparing aqueous solutions of iron(III) nitrate nonahydrate salt [Fe($NO_3$)$_3$.9$H_2O$], antimony salt and platinum salt by adding water and hydrochloric acid and heating the solutions at 100° C.;
  (b) mixing the aqueous solutions formed in step (a) in the required proportion such as herein described to form a mixed solution;
  (c) sonicating the mixed solution formed in step (b) and adding hydrazine during sonication to produce a precipitate;
  (d) centrifuging, washing and drying of the precipitate formed in step (c) to get a γ-ferric oxide based powder.

In another aspect of present invention, antimony salt is incorporated in an oxide, carbonate, nitrate, or any other salt form.

In another aspect of present invention, platinum is incorporated in a metallic form, chloride, nitrate, or any other salt form.

In another embodiment of the present invention, the process of fabricating sensors using the composition comprising the steps of:
  a) mixing the γ-ferric oxide based powder with isopropanol to form a slurry;
  b) taking a substrate and heating it at temperature of 1000° C., for attaching a gold electrode and a platinum wire to the substrate;
  c) taking the slurry as prepared in step (a) and drop coating onto the spinning substrate to make a drop coated substrate;
  d) curing the drop coated substrate at a temperature in the range of 200-450° C.;
  e) inserting a kanthal heating coil inside the drop coated substrate; and,
  f) fixing the sensor-coated substrate on as Transistor Outline (TO) type package by wire bonding/soldering to form a sensor.

In another aspect of the present invention, the sensor is made in the form of a thick or a thin film on substrates and/or in a bulk form.

In another aspect of the present invention, substrates are selected from alumina or insulating materials and are in the form of tube, planar structure or microelectromechanical systems (MEMS) based microheater.

In another embodiment of the present invention, the sensor using the said composition detects 1 ppm and sub-ppm concentrations of acetone in presence of high amount of moisture.

In another embodiment of the present invention, the composition is used in the diagnosis of diabetes and related disorders with abnormal acetone concentration.

Yet another embodiment of the present invention provides a sensor composition for acetone detection in breath for diabetic diagnostics and a process of preparation thereof, which comprises γ-$Fe_2O_3$ about 87.5 to about 95.7 wt %, $Sb_2O_3$ about 2.9 to about 9.9 wt % and Platinum about 0.5 to about 2.6 wt %.

For real-life applications of semiconductor sensors for diabetic diagnostics, they should be sensitive to acetone (breath biomarker of diabetes) of around 1 ppm concentration. Also, they should be selective to acetone in breath and on the top and they should be insensitive or nearly insensitive to high amount moisture present in the breath. The last criterion is difficult to fulfill as semiconductor sensors are notoriously sensitive to moisture.

The present invention provides a composition which satisfies the above criteria and particularly the last criterion which is difficult to meet. As per preliminary studies, sensors fabricated by present inventors using the invented composition show variation in breath acetone level of healthy individuals before and after food. Also, preliminary study shows that the sensors made by using the invented composition can detect high breath acetone level in diabetic patients.

Normally, $Fe_2O_3$ can easily be obtained as α-$Fe_2O_3$. However, it needs tailoring of the processing steps to get $Fe_2O_3$ in "gamma" form. Interestingly, conventional chemical precipitation routes provide α-$Fe_2O_3$, whereas sonochemical method provides nanosized γ-$Fe_2O_3$ because of cavitation, which generates localized high temperature and pressure. The particles of the composition for making sensors should be in the nanosize range for improved sensitivity, response & recovery times which is easily obtained through sonochemical method.

In order to prepare the sensor composition (γ-$Fe_2O_3$ about 87.5 to about 95.7 wt %, $Sb_2O_3$ about 2.9 to about 9.9 wt % and Pt about 0.5 to about 2.6 wt %.), the aqueous solutions of iron salt (Fe($NO_3$)$_3$.9$H_2O$), antimony salt ($SbCl_3$), platinum salt (anhydrous $PtCl_4$) are made by adding hydrochloric acid (HCl) and heating the solution at 100° C. The solutions are mixed in the required proportion and the mixed solution is sonicated and during sonication hydrazine is added to the solution. The precipitate is centrifuged and washed with distilled water and dried in an oven to get γ-$Fe_2O_3$ based powder. However, γ-$Fe_2O_3$ can also be prepared through the methods such as solid-state, soft chemistry and vapour phase methods already reported in the prior art.

The invented composition is used to fabricate thick film, thin film or bulk gas sensors following the techniques known in the art. The sensor platform may be tubular alumina or other insulating substrates, planar alumina or other insulating substrates or MEMS based microheaters/microhotplates. One exemplary technique is described herein.

The γ-$Fe_2O_3$ based powder amounting to about 0.0015 g was mixed with 1 mL of isopropanol to form slurry. About 40 μL of the slurry was taken in a micropipette and then drop coated onto a spinning alumina tube (about 4 mm length, 1.5 mm outer diameter and 1 mm inner diameter) on which two gold electrodes and platinum wires had been placed at each end. The gold electrode and platinum lead wires were attached to the ends of the tubes by curing the system at a high temperature (~1000° C.) before applying the paste. The coated alumina tubes were fired at about 300° C. for 1 h at a heating rate of 50° C./h. Kanthal heating coils were then placed inside the $Al_2O_3$ tubes to produce an optimum operating temperature. The sensor-coated alumina tubes were fixed on a TO (Transistor Outline) type package by wire bonding/soldering. The sensors were initially aged at 250° C. for 72 h to achieve the desired stability before the sensitivity measurements. The electrical resistance, percentage of response, and recovery and response times of the sensors were measured at different temperatures (200 to 350° C.) using a digital multimeter (Agilent U1252A) and a constant voltage/current source (Keithley 228A). The sensors to be measured were placed in the middle of a quartz, tube (2 cm diameter and 10 cm length) and externally connected through a digital multimeter and a constant voltage/current source to record the sensor resistance. The sensors were exposed to vapours of low concentration acetone in air, saturated moisture and vapours of low concentration of acetone in an ambience of saturated moisture at different operating temperatures. The low concentration acetone vapours were prepared by serial dilution method in desiccators, The percentage of response, S (equivalent to sensitivity) is defined as, $$S = \frac{(R_a - R_g)}{R_a} \times 100 \quad (1)$$

where, $R_a$ is the sensor resistance in air at the operating temperature, and $R_g$ is the sensor resistance in the target vapour at the same temperature.

The non-obvious inventive step lies in finding out the composition, which is selective to low concentration of acetone in breath but insensitive to high amount of moisture present in breath. Platinum is one of the noble metal catalysts, which improves the acetone sensitivity of the sensors. However, along with acetone sensitivity, platinum also increases moisture sensitivity. The addition of antimony oxide dramatically lowers the moisture sensitivity without affecting the acetone sensitivity. This happens probably because of the fact that in general, the hydroxides of heavy metals like iron exhibit a tendency to cleave off water and to change into oxides or hydrated oxides, as $O^{2-}$ ions can screen the cations better than $OH^-$ ions. However, in a humid environment, some $OH^-$ ions may get attached to $Fe^{3+}$. In contrast, when antimony ions are present in iron oxide, the $OH^-$ ions should be preferentially attached to antimony ions because antimony ions can expand its coordination number to accept $OH^-$ ions in addition to their already coordinated $O^{2-}$ ions and hence, the incorporation of antimony lowers the moisture sensitivity of $\gamma$-$Fe_2O_3$.

The following examples are given by way of illustration of the working of the invention in actual practice and should not be construed to limit the scope of the present invention in anyway.

EXAMPLE 1

In order to prepare a composition having 5.7 wt % $Sb_2O_3$, 1.4 wt % Pt and 92.9 wt % $\gamma$-$Fe_2O_3$, the following solutions were prepared: a) 2.424 g $Fe(NO_3)_3.9H_2O$ (Merck, 99% purity) in 250 mL distilled water, b) 6.25 g $NH_2NH_2.H_2O$ (Hydrazine) (Qualigens, 99% purity) in 250 mL of distilled water, c) 0.0124 g anhydrous $PtCl_4$ (Merck) in 20 mL distilled water in presence of 2 mL concentrated HCl with continuous stirring for 1 h at 100° C. and d) 0.0046 g $SbCl_3$ (Sigma-Aldrich, 99% purity) in 20 mL of distilled water in presence of 3 mL concentrated HCl with continuous stirring for 1 h at 100° C.

The aqueous solutions of the iron salt, antimony salt, platinum salt were mixed together in a 500 mL beaker and the final volume of the solution was adjusted to 300 mL followed by stirring for 10 min. The solution in the beaker was placed under a sonicator (ultrasonic processor, Sonics, 1500 Watt, model VCF1500) and the probe (diameter ~2 cm) dipping length in the solution was ~4 cm. During the sonication (sonication time 2 h), a 0.5 M hydrazine ($N_2H_4H_2O$) aqueous solution (as prepared above) was added drop-wise to achieve the desired pH ~8 of the solution for complete precipitation. The solution was allowed to cool and at the end of the reaction, a mud coloured precipitate was obtained. After completion of sonication, the obtained particles were separated out by centrifuging the solution at 10,000 rpm for 15 min. The particles were washed several times by centrifuging in distilled water. Finally, the mud coloured powder was dried in vacuum oven at 100° C. the 16 h.

The sensors were fabricated from the synthesized powder as given in the previous section and the gas sensing behaviour was studied as described in the previous section.

The present invention is illustrated in FIGS. 1 and 2 of the drawings accompanying the specification. In the drawings, FIG. 1 represents the response of $\gamma$-$Fe_2O_3$-based sensors of Example 1 towards 1 ppm acetone vapour in air (RH ~45%) and saturated moisture at the operating temperature of 300° C. and FIG. 2 represents the percent response of $\gamma$-$Fe_2O_3$-based sensors of Example 1 towards different concentrations of acetone vapours in air (RH ~45%) at an operating temperature of 300° C.

TABLE 1

Data showing gas sensing characteristics of $\gamma$-$Fe_2O_3$-based sensors towards 1 ppm acetone vapour in air (RH~45%) and 1 ppm acetone vapour in saturated moisture at an operating temperature of 300° C.

| Sensor identification | Percent response (average) towards 1 ppm acetone vapours in air (RH~45%) | Percent response (average) towards 1 ppm acetone vapour in saturated moisture | Response time (average) (s) | Recovery time (average) (s) | Drift (90 days) in response (average) (%) | Drift (90 days) in resistance (average) (%) |
|---|---|---|---|---|---|---|
| Example 1 | 68 | 71 | 06 | 18 | 9.0 | 13.0 |
| Example 2 | 52 | 42 | 06 | 32 | 11.0 | 21.0 |
| Example 3 | 10 | 04 | 04 | 05 | 33.0 | 23.0 |

EXAMPLE 2

In order to prepare a composition having 2.9 wt % $Sb_2O_3$, 1.4 wt % Pt and 95.7 wt % $\gamma$-$Fe_2O_3$, the following solutions were prepared: a) 2.424 g $Fe(NO_3)_3.9H_2O$ (Merck, 99% purity) in 250 mL distilled water, b, 6.25 g $NH_2NH_2H_2O$ (Qualigens, 99% purity) in 250 mL of distilled water, c) 0.0124 g anhydrous $PtCl_4$ (Merck) in 20 mL distilled water in presence of 2 mL concentrated HCl with continuous stirring for 1 h at 100° C. and d) 0.0023 g $SbCl_3$ (Sigma-Aldrich, 99% purity) in 20 mL of distilled water in presence of 3 mL concentrated HCl with continuous stirring for 1 h at 100° C., The aqueous solutions of the iron salt, antimony salt, platinum salt were mixed together in a 500 mL beaker and the final volume of the solution was adjusted to 300 mL followed by stirring for 10 min. The solution in the beaker was placed under a sonicator (ultrasonic processor, Sonics, 1500 Watt, model VCF1500) and the probe (diameter ~2 cm) dipping length in the solution was ~4 cm. During the sonication (sonication time 2 h), a 0.5 M hydrazine ($N_2H_4H_2O$) aqueous solution (as prepared above) was added drop-wise to achieve the desired pH ~8 of the solution for complete precipitation. The solution was allowed to cool and at the end of the reaction, a mud coloured precipitate was obtained. After completion of sonication, the obtained particles were separated out by centrifuging the solution at 10,000 rpm for 15 min. The particles were washed several times by centrifuging in distilled water. Finally, the mud coloured powder was dried in vacuum oven at 100° C. for 16 h.

The sensors were fabricated from the synthesized powder as given in the previous section and the gas sensing behaviour was studied as described in the previous section.

EXAMPLE 3

In order to prepare a composition having 9.9 wt % $Sb_2O_3$, 2.6 wt % Pt and 87.5 wt % $\gamma$-$Fe_2O_3$, the following solutions were prepared: a) 2.424 g $Fe(NO_3)_3.9H_2O$ (Merck, 99% purity) in 250 mL distilled water, b) 6.25 g $NH_2NH_2.H_2O$ (Qualigens, 99% purity) in 250 mL of distilled water, c) 0.0248 g anhydrous $PtCl_4$. (Merck) in 20 mL distilled water in presence of 2 mL concentrated HCl with continuous stirring for 1 h at 100° C. and d) 0.0085 g $SbCl_3$ (Sigma-Aldrich, 99% purity) in 2.0 mL of distilled water in presence of 3 mL concentrated HCl with continuous stirring for 1 h at 100° C.

The aqueous solutions of the iron salt, antimony salt, platinum salt were mixed together in a 500 mL beaker and final volume of the solution was adjusted to 300 mL followed by stirring for 10 min. The solution in the beaker was placed under a sonicator (ultrasonic processor, Sonics, 1500 Watt, model VCF1500) and the probe (diameter ~2) dipping length in the solution was ~4 cm, During the sonication (sonication time 2 h), a 0.5 M hydrazine ($N_2H_4.H_2O$) aqueous solution (as prepared above) was added drop-wise to achieve the desired pH ~8 of the solution for complete precipitation. The solution was allowed to cool and at the end of the reaction, a mud coloured precipitate was obtained. After completion of sonication, the obtained particles were separated out by centrifuging the solution at 10,000 rpm for 15 min. The particles were washed several times by centrifuging in distilled water. Finally, the mud coloured powder was dried in vacuum oven at 100° C. for 16 h.

The sensors were fabricated from the synthesized powder as given in the previous section and the gas sensing behaviour was studied as described in the previous section.

Advantages of the Present Invention:
i. The composition detects acetone at a concentration of 1 ppm and below.
ii. The composition detects low concentration of acetone in an ambience of high moisture.
iii. The composition selectively detects acetone in breath particularly in presence of high moisture in breath, as found from the preliminary studies.
iv. The composition is a potential candidate for a cost-effective, simple, rugged, patient-friendly and non-invasive sensor for diabetic diagnostics from human breath.

REFERENCES

Publications Cited:
1. S. Chakraborty, D. Banerjee, I. Ray, A. Sen, Detection of biomarker in breath: A step towards noninvasive diabetes monitoring, Current Sci., 94, 237 (2008).
2. C. E. F. D. Amaral, B. Wolf, Current development in non-invasive glucose monitoring, Med. Engg. Phys., 30, 541 (2008).
3. C. N. Tassopoulos, D. Barnett, T. R. Frasen, Breath-acetone and blood-sugar measurements in diabetes, Lancet, 293, 1282 (1969).
4. C. Wang, S. T. Scherrer, D. Hossain, Measurements of cavity ringdown spectroscopy of acetone in the ultraviolet and near-infrared spectral regions: potential for development of a breath analyzer, Applied Spectroscopy, 58, 784 (2004).
5. J. M. Sanchez, R. D. Sacks, GC analysis of human breath with a series-coupled column ensemble and a multibed sorption trap, Anal. Chem., 75, 2231 (2003).
6. Q. Zhang, P. Wang, J. Li, X. Gao, Diagnosis of diabetes by image detection of breath using gas-sensitive laps, Biosens Bioelect., 15, 249 (2000).
7. D. Chen, X. Hou, T. Li, L. Yin, B. Fan, H. Wang, X. Li, H. Xu, H. Lu, R. Zhang, J. Sund, Effects of morphologies on acetone-sensing properties of tungsten trioxide nanocrystals, Sensors and Actuators B 153, 373 (2011).
8. X. Cheng, Y. Xu, S. Gao, H. Zhao, L. Huo, Ag nanoparticles modified $TiO_2$ spherical heterostructures with enhanced gas-sensing performance, Sensors and Actuators B 155, 716 (2011).
9. R. C. Biswal, Pure and Pt-loaded gamma iron oxide as sensor for detection of sub ppm level of acetone, Sensors and Actuators B 157, 183 (2011).
10. P. Sun, L. You, D. Wang, Y. Sun, J. Ma, G. Lu, Synthesis and gas sensing properties of bundle-like $\alpha$-$Fe_2O_3$ nanorods, Sensors and Actuators B 156, 368 (2011).
11. J. Shi, G. Hua, Y. Sun, M. Geng, J. Wu, Y. Liu, M. Ge, J. Tao, M. Cao, N. Dai, $WO_3$ nanocrystals: synthesis and application in highly sensitive detection of acetone, Sensors and Actuators B 156, 820 (2011).
12. D. Chen, J. Xu, Z. Xie, G. Shen, Nanowires assembled $SnO_2$ nanopolyhedrons with enhanced gas sensing properties, ACS Appl. Mater. Interfaces 3, 2112 (2011).
13. M. Righettoni, A. Tricoli, S. E. Pratsinis, Thermally stable, silica-doped $\epsilon$-$WO_3$ for sensing of acetone in the human breath, Chem. Mater., 22, 3152 (2010).
14. S-J. Chang, T-J. Hsueh, I-C. Chen, S-F. Hsieh, S-P. Chang, C-L. Hsu, Y-R. Lin, B-R, Huang, Highly Sensitive ZnO nanowire acetone vapor sensor with Au adsorption, IEEE Transactions on Nanotechnology, 7, 754 (2008).

15. Q. Qi, T. Zhang, L. Liu, X. Zheng, Q. Yu, Y. Zeng, H. Yang, Selective acetone sensor based on dumbbell-like ZnO with rapid response and recovery, Sensors and Actuators B 134, 166 (2008).
16. E. Reziescu, C. Doroftei, N. Rezlescu, P. D. Popa, Preparation, structure and gas-sensing properties of $\gamma$-Fe$_2$O$_3$ and $\gamma$-Fe$_2$O$_3$TiO$_2$ thick films, Phys. Stat. Sol. (a) 205, 1790 (2008).
17. M. Yang, L. Huo, H. Zhao, S. Gao, Z. Rong, Electrical properties and acetone-sensing characteristics of LaNi$_{1-x}$Ti$_x$O$_3$ perovskite system prepared by amorphous citrate decomposition, Sensors and Actuators B 143, 111 (2009),
18. Y. Zeng, T. Zhang, M. Yuan, M. Kang, G. Lu, R. Wang, H. Fan, Y. He, H. Yang, Growth and selective acetone detection based on ZnO nanorod arrays, Sensors and Actuators B 143, 93 (2009).
19. L. Wang, A. Teleki, S. E. Pratsinis, P. I. Gourna, Ferroelectric WO$_3$ nanoparticles for acetone selective detection, Chem. Mater., 20, 237 (2008).
20. M. Righettoni, A. Tricoli, S. E. Pratsinis, Si:WO$_3$ Sensors for highly selective detection of acetone for easy diagnosis of diabetes by breath analysis, Anal. Chem., 82, 3581 (2010).

The invention claimed is:

1. A composition for acetone detection, wherein the said composition comprises: (a) $\gamma$-ferric oxide ($\gamma$-Fe$_2$O$_3$), in the range of 87.5-95.7 wt %, (b) antimony (Sb) salt, in the range of 2.9-9.9 wt %, and (c) platinum (Pt) in the range of 0.5-2.6 wt %.

2. The composition as claimed in claim 1, wherein antimony salt is incorporated in an oxide, carbonate, nitrate, or any other salt form.

3. The composition as claimed in claim 1, wherein platinum is incorporated in a metallic form, chloride, nitrate, or any other salt form.

4. A process of preparing the composition as claimed in claim 1, wherein the composition is prepared through sonochemical method comprising the steps of:
    (a) preparing aqueous solutions of iron(III) nitrate nonahydrate salt [Fe(NO$_3$)$_3$.9H$_2$O], antimony salt and platinum salt finally decomposes to metallic platinum by adding water and hydrochloric acid and heating the solutions at 100° C.;
    (b) mixing the aqueous solutions formed in step (a) in the required proportion such as herein described to form a mixed solution;
    (c) sonicating the mixed solution formed in step (b) and adding hydrazine during sonication to produce a precipitate;
    (d) centrifuging, washing and drying of the precipitate formed in step (c) to get a $\gamma$-ferric oxide based composition.

5. The process of preparing the composition as claimed in claim 4, wherein antimony salt is incorporated in an oxide, carbonate, nitrate, or any other salt form.

6. The process of preparing the composition as claimed in claim 4, wherein platinum is incorporated in a metallic form, chloride, nitrate, or any other salt form.

7. A process of fabricating sensors using a composition comprising (a) $\gamma$-ferric oxide ($\gamma$-Fe$_2$O$_3$), in the range of 87.5-95.7 wt %, (b) antimony (Sb) salt, in the range of 2.9-9.9 wt %, and (c) platinum (Pt) in the range of 0.5-2.6 wt %, the process comprising the steps of:
    a) mixing the $\gamma$-ferric oxide based composition with isopropanol to form a slurry;
    b) taking a substrate and heating it at temperature of 1000° C. for attaching a gold electrode and a platinum wire to the substrate;
    c) taking the slurry as prepared in step (a) and drop coating onto the spinning substrate to make a drop coated substrate;
    d) curing the drop coated substrate at a temperature in the range of 200-450° C.;
    e) inserting a kanthal heating coil inside the drop coated substrate; and,
    f) fixing the sensor-coated substrate on a Transistor Outline (TO) type package by wire bonding/soldering to form a sensor.

8. The process as claimed in claim 7, wherein the sensor is made in the form of a thick or a thin film on substrates and/or in a bulk form.

9. The process as claimed in claim 7, wherein the substrate is selected from alumina or insulating materials and are in the form of tube, planar structure or microelectromechanical systems (MEMS) based microheater.

10. The process as claimed in claim 7, wherein the fabricated sensors detects 1 ppm and sub-ppm concentrations of acetone in presence of high amount of moisture.

11. The composition as claimed in claim 1, wherein the composition is used in fabricating sensors for the diagnosis of diabetes and monitoring diabetic patients with abnormal acetone concentration.

12. The composition as claimed in claim 1, wherein $\gamma$-Fe$_2$O$_3$ is prepared through sonochemical or any other synthesis route.

* * * * *